US009775565B1

(12) United States Patent
Berg-Neuman et al.

(10) Patent No.: US 9,775,565 B1
(45) Date of Patent: Oct. 3, 2017

(54) DEVICE AND SYSTEM FOR MONITORING OPERATOR BIOMETRIC CONDITION AND BLOOD ALCOHOL PRESENCE TO PREVENT DRIVING OF A VEHICLE BY AN ALCOHOL OR OTHERWISE IMPAIRED OPERATOR

(71) Applicants: Tammy Berg-Neuman, Hillsboro, MO (US); James L Gowan, Hillsboro, MO (US)

(72) Inventors: Tammy Berg-Neuman, Hillsboro, MO (US); James L Gowan, Hillsboro, MO (US)

( * ) Notice: Subject to any disclaimer, the term of this patent is extended or adjusted under 35 U.S.C. 154(b) by 0 days.

(21) Appl. No.: 14/947,253

(22) Filed: Nov. 20, 2015

Related U.S. Application Data

(60) Provisional application No. 62/082,793, filed on Nov. 21, 2014.

(51) Int. Cl.
A61B 5/00 (2006.01)
A61B 5/1477 (2006.01)
(Continued)

(52) U.S. Cl.
CPC ........ *A61B 5/6893* (2013.01); *A61B 5/14521* (2013.01); *A61B 10/0064* (2013.01);
(Continued)

(58) Field of Classification Search
CPC G08B 23/00; G06F 7/00; G06F 17/00; A61B 5/00; A61B 5/1477
See application file for complete search history.

(56) References Cited

U.S. PATENT DOCUMENTS 5,465,713 A * 11/1995 Schoendorfer ........ A61B 5/411
600/346
5,793,292 A * 8/1998 Ivey, Jr. ................... A61B 5/18
340/576

(Continued)

*Primary Examiner* — Yonel Beaulieu
*Assistant Examiner* — Martin Weeks
(74) *Attorney, Agent, or Firm* — Todd S. Parkhurst; Greensfelder, Hemker & Gale, PC

(57) ABSTRACT

A new system monitors ethanol alcohol levels of a vehicle operator by collecting sweat from the operator's hands, and detecting the presence, if any, of ethanol in the sweat. The system can then be used, if ethanol is present, to take action, such as immobile vehicle disablement, in the event of intoxication caused by an impermissibly high levels of ethanol of the operator. The system includes devices, referred to as pods in the description, which are sweat-collecting devices that are attached to the steering wheel of the vehicle. If the measurable ethanol in collected moisture from the operator's hands exceeds a preset threshold, the system could be configured to warn the operator to park the vehicle thereafter to disable operation of the vehicle, but if the operator does not so discontinue operation of the vehicle hazard warning lights and audible warnings within and without the vehicle will be activated alerting near vehicles of a dangerous vehicle being operated in close proximity. Likewise the new system monitors for pulse rate and oxygen levels of the operator can be used to recommend operator action when the pulse rate and/or oxygen levels are outside of the normal range for an operator. When the pulse rate and or oxygen levels of the system are outside of the normal parameters for an operator, the system will warn the operator to park the vehicle and thereafter to disable operation of the immobile vehicle, but if the operator does not so discontinue operation of the vehicle the hazard warning lights, on board video, and audible warnings within and without the vehicle will be activated alerting near vehicles of a dangerous (Continued)

vehicle being operated in close proximity, and alarms will be sent to real time recording and monitoring devices.

13 Claims, 8 Drawing Sheets

(51) Int. Cl.
    *G06F 7/00*     (2006.01)
    *G06F 17/00*     (2006.01)
    *B60W 40/08*     (2012.01)
    *A61B 10/00*     (2006.01)
    *A61B 5/145*     (2006.01)

(52) U.S. Cl.
    CPC ..... *B60W 40/08* (2013.01); *A61B 2010/0083* (2013.01); *B60W 2040/0836* (2013.01); *B60W 2422/50* (2013.01); *B60W 2540/26* (2013.01); *B60W 2600/00* (2013.01)

(56) References Cited

U.S. PATENT DOCUMENTS

| | | | | |
|---|---|---|---|---|
| 6,200,459 | B1* | 3/2001 | Vadgama | G01N 27/40 204/415 |
| 2004/0083031 | A1* | 4/2004 | Okezie | A61B 5/145 701/1 |
| 2007/0144812 | A1* | 6/2007 | Stewart | B60K 28/063 180/272 |
| 2008/0306362 | A1* | 12/2008 | Davis | A61B 5/14521 600/307 |
| 2012/0270205 | A1* | 10/2012 | Patel | G01N 27/126 435/5 |
| 2013/0027209 | A1* | 1/2013 | Carroll | A61B 5/14546 340/576 |
| 2014/0058622 | A1* | 2/2014 | Trombley | B60R 1/00 701/33.2 |
| 2014/0276090 | A1* | 9/2014 | Breed | A61B 5/18 600/473 |

* cited by examiner

POD P1 PLAN VIEW

POD P1 SIDE VIEW

POD P1 VAPOR END VIEW

POD P1 TRANSVERSE CROSS SECTION

SECTION A-A

BAC and BIOMETRIC COLLECTOR

BBC 1

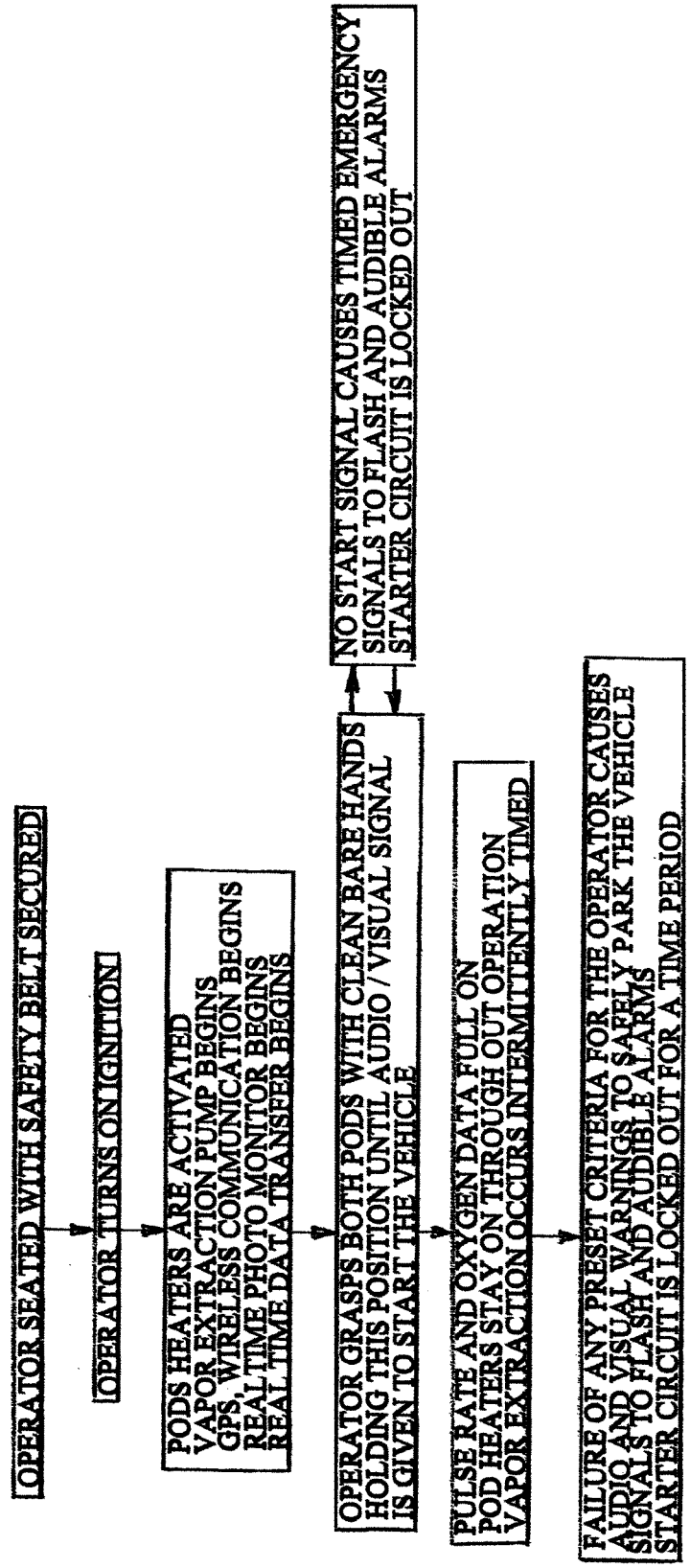

DEVICE AND SYSTEM FOR MONITORING OPERATOR BIOMETRIC CONDITION AND BLOOD ALCOHOL PRESENCE TO PREVENT DRIVING OF A VEHICLE BY AN ALCOHOL OR OTHERWISE IMPAIRED OPERATOR

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

BACKGROUND

Field of the Invention

The presently described invention generally relates to devices for monitoring of epidermal blood alcohol, and biometric anomaly's that is, ethanol levels, pulse rate, and oxygen levels of a vehicle operator and, more particularly, to a system including devices of this character for taking action, such as vehicle start disablement, in the event of impairment caused by impermissibly high levels of ethanol or biometric anomalies of the operator.

SUMMARY

In the operation of motor vehicles of many types, including automobiles ("cars"), trucks, buses and trains, and public transportation vehicles and other vehicles, it is desired to prevent vehicle operators from operating in impaired state resulting from high or impermissible levels of consumed alcohol or alcoholic beverages. This type of alcohol is referred to simply as spirits, ethanol or ethyl alcohol, or drinking alcohol. This is the principal alcohol found in alcoholic beverages, and is produced by the fermentation of sugars by yeasts. It is well known that ethanol can cause alcohol impairment when consumed in sufficient quantity. Ethyl alcohol (ethanol) has the structural formula $CH_3CH_2OH$, often abbreviated as $C_2H_5OH$ or $C_2H_6O$ or ETOH.

It is equally necessary that vehicle operators do not operate a vehicle when their abnormal biometric anomalies, or distractive driving is demonstrated during operation of the vehicle.

The new system described here, as installed in a vehicle, monitors the driver so as to determine the presence, and level of ethanol (if present) in palmar sweat. The system includes sweat-responsive devices, as may also be called sweat-collecting devices, attached to the steering wheel of the vehicle. The system determines if the measurable ethanol in collected moisture from the driver's hands exceeds a preset threshold, and is configured to prohibit the operator from starting the vehicle or instructing the operator to park the vehicle shortly thereafter and cease operation of the vehicle. Other functions are described.

For example, the invention provides an alcohol ignition interlock system and method by which an operator under the influence of alcohol is prevented from starting and operating the immobile vehicle equipped with the system.

The new system is deemed effective for use by operators who are prior offenders being assessed for alcohol dependence or addiction, wherein data provided by the system is helpful to alcohol treatment clinics and courts, and helpful to these prior offenders in aiding them in developing understanding of their self-control and progress, while also enforcing compliance.

A vehicle epidermal and biometric collecting and data transmittal aspect of the system device provides capability to continuous record and transmit data, and to make use of that data for control features of the system, by receiving and monitoring palmar sweat which unavoidably includes low concentrations of ethanol which, by the use of sweat-responsive features of the invention, can be extracted as vapor that can be subjected to analysis in the system as an indication of the level of blood alcohol content of the driver.

The system can indicate consumption and the presence of BAC by measurement of Epidermal Alcohol Content (EAC), as determined by an ethanol level measuring device responsive to ethanol vapor extracted from the pod devices, which are ethanol vapor collection devices of the invention. The ethanol level measuring device is connected to the pods to receive the ethanol vapor, if present. The measuring device is separated from the pods, and has associated with it interface circuit connections with the vehicle's starting ignition circuits, and with warning lights such as the vehicle flasher lights and certain circuit-controlled locks to prevent driving of the vehicle, if that is deemed a necessary result. The interface can also cause a digital image and sound recording of the driver to be taken, and provide storage of data relating to operation, location of the vehicle, and provide aural messages to inform the operator, such as warnings and/or the need to park the vehicle.

Other functions are described in the following description.

In addition to the ability of this system to detect levels of ethanol in the sweat and vapor of the operator the system can also detect and evaluate pulse rate, oxygen level, and operator distractions, such as texting, all of which are recorded real time as data, sound, and video as well as activating visual and audio caution signals and alarms within, and without, the vehicle being operated.

DRAWINGS

FIG. 1 is a frontal view of a representative steering wheel of a vehicle, such as that of some arbitrary automobile, upon which is mounted ethanol monitoring device for monitoring the presence of ethanol in the body, and biometrics, of a operator using the steering wheel, in accordance with the present invention.

FIG. 2 is a top plan view of a device referred to herein as a "pod" representative of two such devices attached to a steering wheel such as typified by FIG. 1, the device being intended to monitor the biometrics and hand sweating by the operator gripping the steering wheel in skin contact with the heated pods, and by such sweating to capture ethanol vapor in responses to the presence of ethanol in the body of the operator.

FIG. 8 is a flow chart of events and consequences.

Corresponding characters indicate corresponding elements in different views of the drawings.

DESCRIPTION OF PRACTICAL EMBODIMENTS

Figure 1:
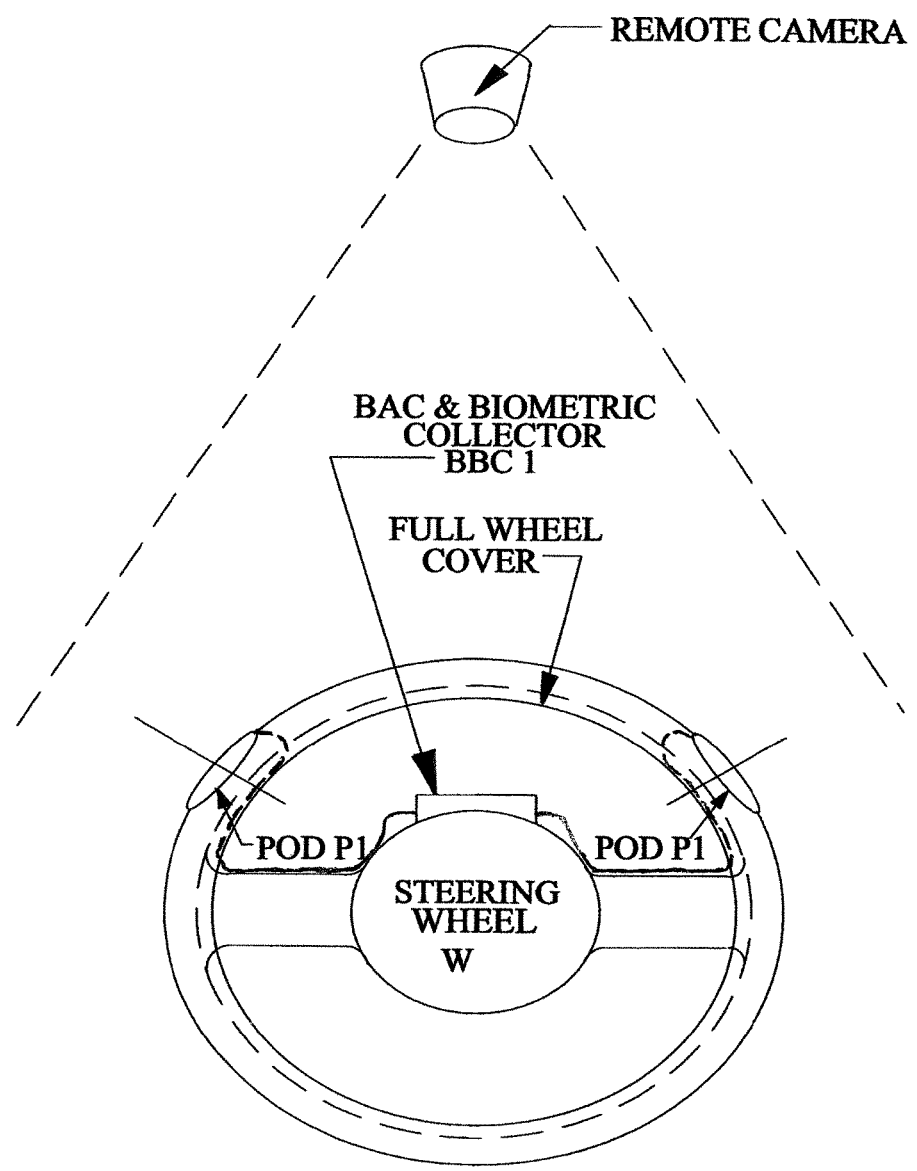
Figure 2:
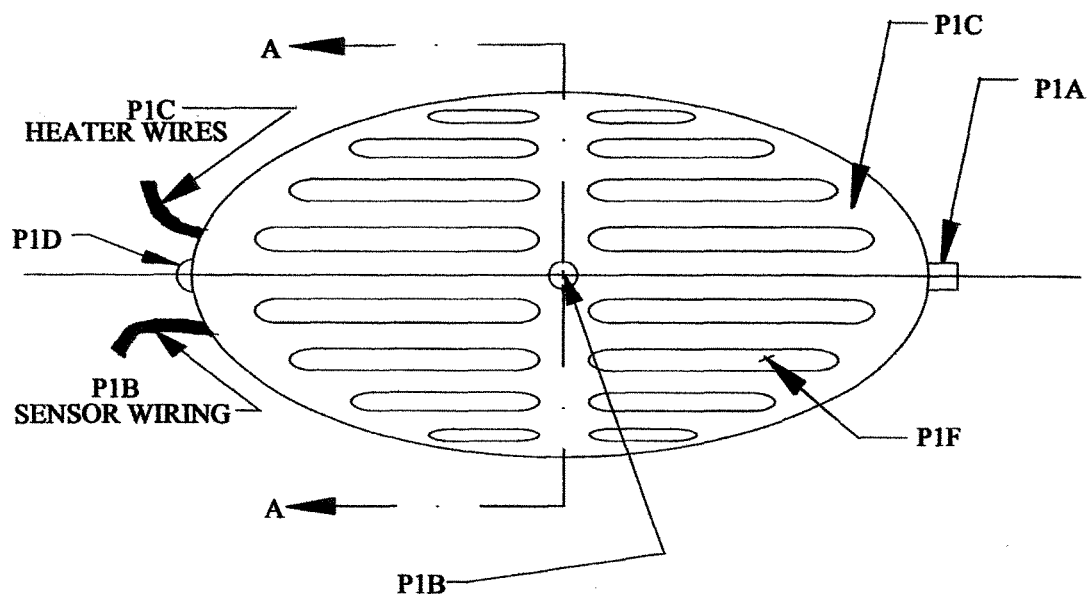
Figure 3:
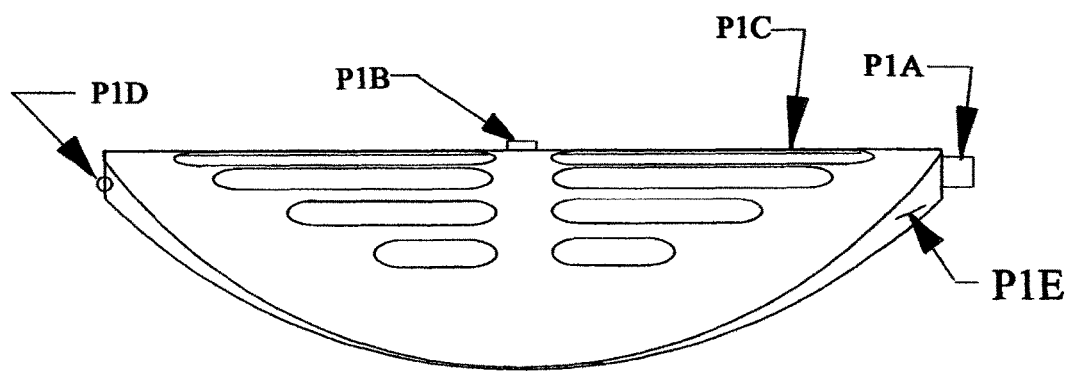
FIG. 3 is side elevation view of the device of FIG. 2.
Figure 4:
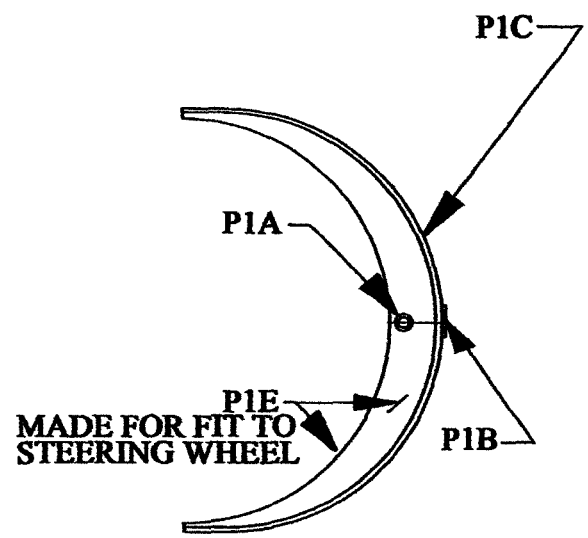
FIG. 4 is an end view of the device of FIG. 2.
Figure 5:
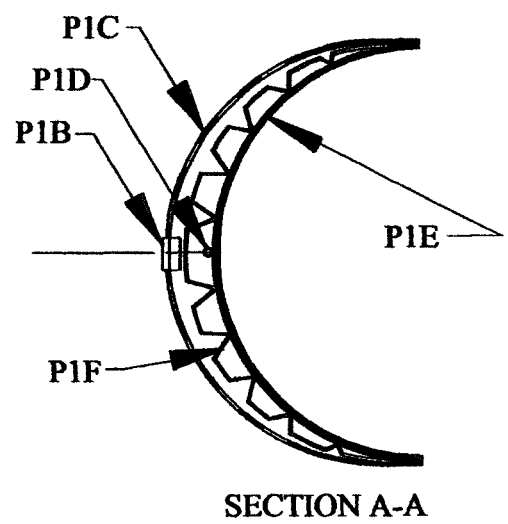
FIG. 5 is a transverse cross section of the device of FIG. 2, taken along line A-A of FIG. 6 is a orthographic projection of the P1 pod assembly.
Figure 6:
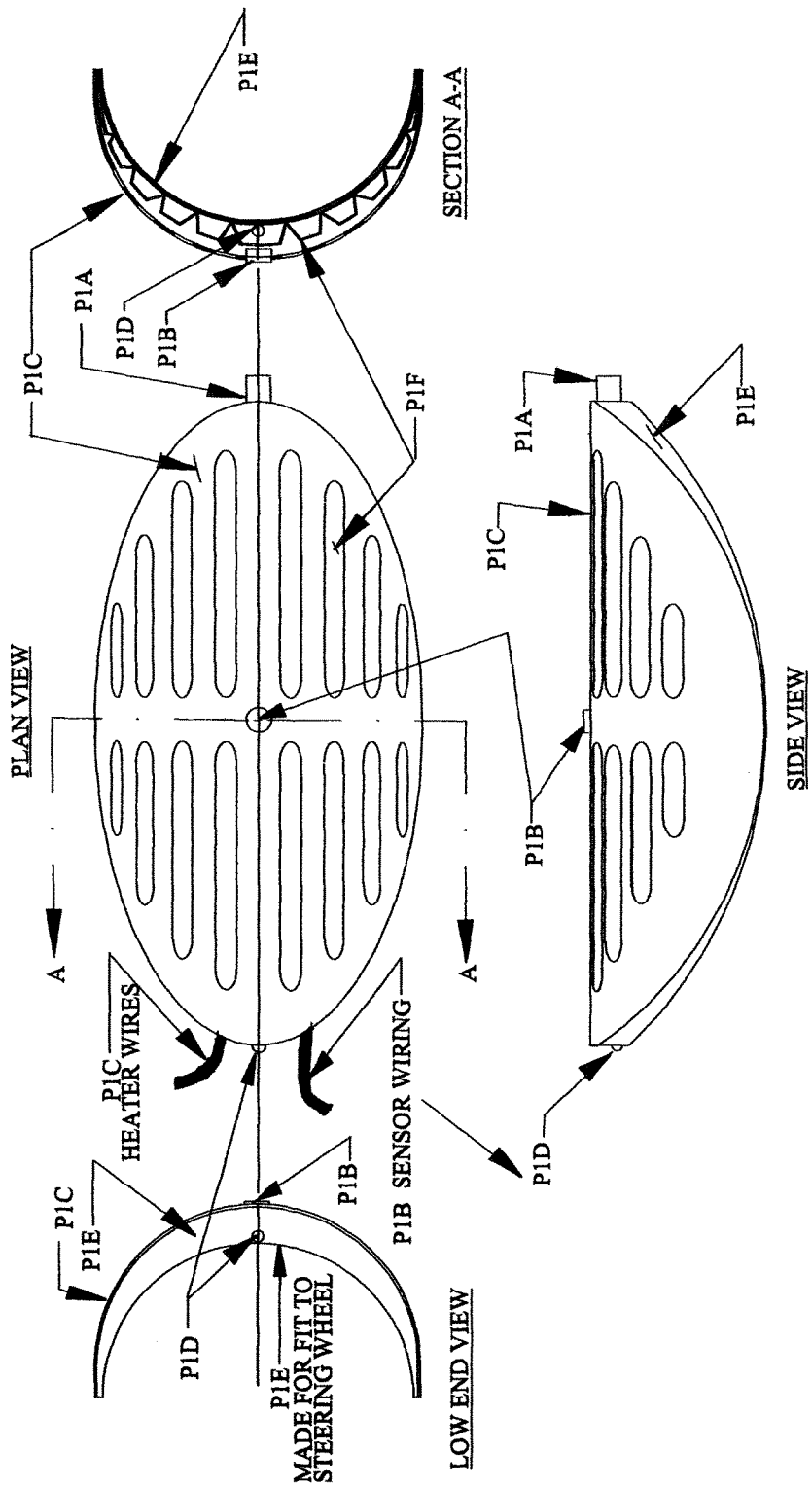
Figure 7:
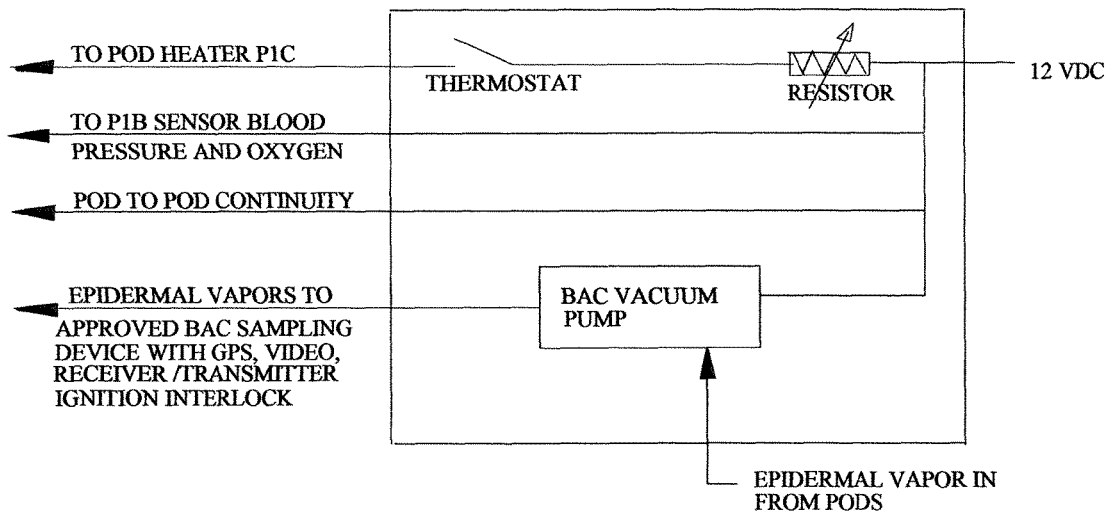
FIG. 7 is a BAC and Biometric collector system.

Referring to the drawings, illustrated generally is an embodiment of the new ethanol monitoring device for monitoring alcohol levels of a vehicle operator and, more particularly, to such a device for taking action, such as immobile vehicle disablement, in the event of a transdermally sensed impermissibly high BAC of a driver or other operator biometric impairments.

Key features of the alcohol monitoring device include incorporating sweat collection for the operator's hands, and which devices are secured to the vehicle steering wheel. These devices are intended to combine ethyl alcohol (often called ethanol) collection while the operator steers using normal operation of the steering wheel, which is not replaced but, with addition of the pod-like monitoring devices, here referred to as pods, provides a location for collection of normal palmar sweat which may include ethanol, if present, excreted by sweating of the operator's hands. Beyond sensing of ethanol, other parameters such as the operator's oxygen level and pulse rate can also be measured by sensing devices, as later explained in this description.

The system is also capable to sense the operator's pulse rate and oxygen level in data to be monitored, for that data can signal a operators distress or a change in physiological parameters that should be useful. Because skin contact is provided by the system, interruption in electrical conductivity resulting from the act of lifting either hand from the steering wheel can be useful for signaling, for example, that the operator is not driving with both hands, as may connote so-called texting or other inadvisable use of hand-held electronic devices such as digital telephones or web browsers.

Data that can be provided and saved in a system of the invention may include vehicle location, as indicated by optional use of GPS (Global Positioning System) location monitoring technology (not shown).

For contact with hands of the operator, sweat-collecting pods are attached to the steering wheel, (or control bar of a motorcycle for example) of the vehicle without modifying or damaging the steering wheel, or control bar, yet enabling the operator to be in hand contact with the pods during normal operation of the vehicle. Each pod location is convenient for the operator to place the hands while operating the vehicle by steering wheel control. When the operator's hands are in contact with the pods, the operator is monitored periodically for ethanol expressed even in the low levels of sweat present on the palms of the operator's hands.

In use of the system, reliability is obtained because the shape and palm-adaptive geometry of each pod provides reliable contact with the palmar skin of the operator, although the skin across the palm of an operator may be of varied nature, or may be calloused, rough, or uneven, being defined of course by body size and habitus which are normal or typical physical characteristics of a driver.

The system's pods are not only sweat-receiving devices for collecting sweat. As noted, the pods also can be configured to sense the operator's pulse rate and oxygen level in data to be monitored, for that data can signal a operators distress or a change in physiological parameters that should be useful.

Because skin contact is provided by the system, change in electrical conductivity resulting from the act of lifting either hand from the steering wheel can be useful for signaling, for example, that the driver is not driving with both hands, as may connote so-called texting or other inadvisable use of hand-held electronic devices such as digital telephones or web browsers. Data that can be provided and saved in a system of the invention may include vehicle location, as indicated by optional use of GPS (Global Positioning System) location monitoring technology.

The system includes a pair (or more) of sweat-responsive devices, attached to the steering wheel or steering bar of the vehicle, are configured to sense the operator's pulse rate and oxygen level in data to be monitored, for that data can signal a driver's distress or a change in physiological parameters that should be useful. Because skin contact is provided by the system, change in electrical conductivity resulting from the act of lifting either hand from the steering wheel can be useful for signaling of that act.

Data that can be provided and saved in a system of the invention may include vehicle location, as indicated by optional use of GPS (Global Positioning System) location monitoring technology.

Referring to the drawings, an important feature of the new system is the adaptive use of the existing steering wheel as designated W in FIG. 1. To the peripheral rim of the steering wheel are secured pods P1 applied to two selected wheel peripheral portions. The wheel portions, which are arcuate segments of wheel W, are those which may be normally gripped by the opposite hands, for example, at opposite left and right steering wheel positions. These may be as according to clock hour positions. Ten and two o'clock, or nine-and-three o'clock, or eight-and-four o'clock are illustrative of steering wheel portions for either hand or both hands. Devices P1 are thus to be gripped either by an operator's left and right hands, that is, normally by both hands except that a operator may sometimes lift one hand from the wheel for a control adjustment, for example, or to change transmission ratios, and so forth.

Pods P1 are each of unitary, integral self-contained character. Each has a single housing 100 shown FIGS. 1, 2, 3, 4, 5, and 6 that is sized peripherally along the steering wheel such that a substantial extent of each palm of the operator will peripherally overly a substantial extent of a peripheral sensing surface of the respective distinct housing portions, which are dimensionally configured to be in contact with skin of a substantial extent of each palm. Although the pods P1 may be, as indicated, located upon preferred segments of wheel W, a good arrangement is separate pod housings for the operator's opposed hands wherein the housing P1 is elongated along the surface of the steering wheel W, being dimensionally configured for contact with skin of a substantial extent of each palm of the operator.

The new system is best configured to be added to a conventional vehicle, whether it may be a car, truck, van, road or utility vehicle, or industrial equipment, or a boat, in any of which a operator is to be monitored for ethanol consumption and BAC by measurement of epidermal alcohol content (EAC) as ethanol in palmar sweat captured by pod devices P1 affixed to the steering wheel. The system can be thereby installed on an existing vehicle in such a way as to maintain the capabilities and uses of the vehicles for operators who do not require monitoring. It is preferred that the pod will be applied to the steering wheel to avoid need for replacement or destructive modification of the steering wheel or without changing the structure of the steering wheel.

Securement of pod P1 to the steering wheel is the following:

Each pod P1 is securely fastened, in a variety of chosen positions, for rigid attachment to the steering wheel W, without drilling, pinning, or otherwise penetrating the original surface of the steering wheel. One method of achieving this attachment is by utilizing a polymer wrap that clings tightly to the contour of the steering wheel positions selected while allowing an opening or openings for each pod to be in contact with the operator's palmar skin of the hands. Such polymer wrap shall be applied in a manner so that no arcural movement with respect to the steering wheel can occur when reasonable force is applied by the operator of the vehicle. Further no application of the pod or polymer wrap fastening to the steering wheel shall impede the operation of vehicle control or safety devices on the steering wheel by the operator.

An alternate way of securement of pod P1 to the steering wheel is the following: Each pod P1 is securely fastened, in a variety of chosen positions, for rigid attachment to the steering wheel W, without drilling, pinning, or otherwise penetrating the original surface of the steering wheel, another method of achieving this attachment is by utilizing a full steering wheel polymer wrap that clings tightly to the contour of the steering wheel positions selected while allowing an opening or openings for each pod to be in contact with the operator's palmar skin of the hands. Such polymer wrap shall be applied in a manner so that no arcural movement with respect to the steering wheel can occur when reasonable force is applied by the operator of the vehicle. Further no application of the pod or polymer wrap fastening to the steering wheel shall impede the operation of vehicle control or safety devices on the steering wheel by the operator.

In one aspect of the invention, each of pods P1 is covered by what may be termed a palm shield P1C, which is of slotted character, being provided with an array of closely spaced, generally parallel slots, although the slots or other apertures may be other than parallel. As shown, the slots extend in the direction along the periphery of wheel W, and yet may be transverse to the periphery, or may be replaced by an array of apertures, if they prove to be effective, of circular or other shape. The slots are of varying length so that the longest slots lie atop the shield but are shorter as they approach the lateral edges of the shield, i.e., in a direction transverse to the periphery of wheel W.

Shield P1C might best be formed of a relatively thin layer of metal such as stainless steel, or a base metal carrying an ionized coating, or it may be formed of a heat resisting polymer or another alloy, such as one of the aluminum alloys. Its thickness is most preferably in the range of about 0.5 mm to about 1.5 mm so as to provide strength and resistance to bending or deformation, and yet being capable of being formed in a machining, molding, shaping or manufacturing process during the manufacture of the pod.

The palm shield P1C provides a curved upward surface having geometry for extending smoothly around steering wheel W to provide not only a resting surface, where the operator can comfortably maintain steady and reliable contact while gripping the steering wheel, yet with its slots being capable of admitting moisture from normal or heat-induced palm sweating.

Slots are arranged in two groups of closely spaced character, in general parallel configuration. There are here illustrated left and right such groups, located to opposite sides of a sensor P1B which can be a commercially available pulse-type oxygen and pulse rate sensor of the type used in watches and medical devices that provide output signals indicating oxygenation values and pulse rate (heart rate) so that these data about the driver can be obtained by simple contact with the pod shield. It may be found sufficient for a single such sensor to be used, that is, connected to, or located on, only one of pods P1, such as pod P1 for the left hand. Wiring connection for sensor P1B is not shown for simplicity of view.

Moisture from hand sweat, which gives rise to vapor that can carry ethanol, is drawn into the pods P1 by partial pressure caused by a vacuum source discussed later. The moisture is captured by HEPA media layer within the pods. Beneath the palm shield P1C of each pod lays such a HEPA filter layer P1F. The acronym HEPA stands for "high-efficiency particulate air" filtration, meaning a type of filter media of commercially available material useful to filter gases or other gaseous media having particulate matter or vapor, including water vapor and/or water vapor mixed with ethanol vapor mixed with water vapor. As is known by those skilled in the art, HEPA media must meet standards of efficiency such as those set by the United States Department of Energy (DOE). The HEPA filter layer P1F is shown in cross-section, which illustrates that this form of filter layer has a general pleated character having raised portions of frustoconical cross section linked at bases such as at P1E to provide a continuous layer through which a mix of moisture and ethanol, if any, will result from the natural action of sweating at the palmar surface.

Filter media P1F lies upon a back face P1E of the pod. The back face may be metal or other suitable material. It is appropriately shaped for steering wheel conformance, being a shape in which there is a line of arc forming a section of a circle that lies upon a desired portion of the periphery of steering wheel W. The pod geometry is in general sized to fit conformingly to a typical steering wheel. Different pod sizes or geometries of the wheel-conforming back of the pod can conform or adapt to different types or sizes or diameters of steering wheels.

Each pod P1 includes an internal thermostatically controlled heater or heating array P1C under the skin contact portions of the pod shields to provide mild warming of skin contact portion by a sufficient amount as to cause palmar skin of the operator to sweat by an increased degree so that the pods assuredly will be exposed to sweat of the operator's hands. The heater's thermostatic control can be internal and temperature responsive, according to the operator's compartment (so-called "cabin") preference, so as to be warm enough for increased sweating even if cabin temperature may be a cooler than an expected temperature range. Thus, epidermal alcohol content (EAC) of ethanol from the operator's hands can be collected, when present in palmar sweat, even if there is a below-normal cabin temperature range.

Vapor emission of sweat from the hands is thereby collected on the face of HEPA layer P1F by deposit of moisture there, which moisture may contain any epidermal ethanol emissions in palmar sweat. Then, because of a vacuum line connected at a port, the vapor resulting from deposit of moisture on HEPA filter is drawn off by the vacuum (partial pressure) line.

At one end of each pod, as noted above, a vacuum port P1A is connected to a thin flexible conduit at lower gas pressure as a vacuum source periodically conveys sweat vapor to ethanol sensing device portions of the new system, where ethanol vapor is sensed and by which BAC can be determined by the control module.

A moisture weep hole P1D at the opposite end of each pod can be provided to allow for residual moisture in the pod to drain or be wicked away after use of the system. For that purpose, the weep hole may contain a moisture-conducting wick. A one-way check valve optionally can be provided to prevent flow of such moisture in a wrong direction from the weep hole, so that during normal operation moisture is only drawn off, as in vapor form recovered from the HEPA media, and provided through the vacuum port for analysis of any ethanol content.

Now consider the system components for measuring ethanol content of the vapor drawn off by the vacuum port P1A. The ethanol content vapors from vacuum port P1A are conveyed to a commercially available state of the art BAC analysis system. Some of the most reliable systems to date are the SCRAM type device and the SOBERLINK. Both of these devices could be used in conjunction with the POD P1 system described herein.

The ethanol sensing module may be one of many state of the art commercial ethanol sensing devices that have wireless real time Bluetooth type, photo video, data transmittal, and GPS capabilities.

It is now understood that the vehicle operator can by such convenient and comfortable hand contact with the pods be monitored by extracting ethanol emitted epidermally through the skin of either hand of a vehicle operator when either or both hands are in contact with the pod device when it is installed on a peripheral portion of the steering wheel of the vehicle, because each pod is a key module that can be optionally installed in the vehicle for full-time use by the driver for whom BAC is to be monitored. When installed as part of a system, the pod devices can cause the system to take action, such as immobile vehicle (disablement) ignition prevention and data reporting or recordation, in the event of an impermissibly high driver BAC.

The system can be used to determine if the operator lifts either hand from the pod devices. In that regard, the system can be configured to take electronic photo images of video of the vehicle operator when that operator removes the hand or hands from pod P1 contact, such as if the operator is using an electronic device for texting or using a hand for activities that may degrade driving, such as operating other equipment or carrying out other activities with the free hand. Such images can later be used to verify activity of the operator.

Electronic photo images provided by system can be used also for verification of the identity of the operator, as when driving activity is initiated by a operator.

Useful other results are obtained. Operation of the vehicle by an impaired operator can be used to activate vehicle emergency lights and also sound an operator alert requesting the operator to safely park the vehicle within a short time. The system can also send an alarm to a remote monitoring facility so as to reactivate the ignition interlock system when authorized. As described below, the pod devices can also be configured to measure the operator pulse rate and oxygen levels. These values can be sensed to determine if the operator were to experience physiological changes that might signal distress or impairment, so that appropriate action can be required by the system.

Data obtained by the pod devices is highly useful for a variety of purposes such as those indicated and for other purposes. In addition, the system makes possible for communications and data to be stored in real time, so as to be available to an authorized off-site monitoring location during vehicle operation, and for later analysis. The data can also be available for communication to the operator when needed, e.g., for proof and for education, and to assist self-control and progress in a drinking control program monitored by court or clinic.

In operation, the system having the device can give display an instructive warning to the operator if BAC goes too high or biometrics are out of permissible range, providing an announcement to the operator of a period in which the operator is given enough time to park the vehicle safely. Then, after a predetermined delay period, the system can be configured to cause shutdown of the immobile vehicle. In that case, immobile shutdown of the vehicle can prevent the operator from restarting the vehicle until the system is reset by an authorized person or by radio message to the system.

The monitoring device development makes possible many useful functions. A vehicle equipped with the system could not be started if the monitoring device sensing elements sense driver BAC such as >0.05 BAC (% by vol.), for example. When the vehicle is in normal operation, BAC ethanol level is monitored every 15 min. for example, or more frequently if BAC trends higher but less frequently if BAC trends lower. If the monitoring device senses that operator BAC exceeds a preset threshold, system circuits signal the operator, as by LED display which can be built into the wheel wrapping or provided in a suitable display structure, to quickly and safely park the vehicle. The operator is thereby provided a time interval in which to safely leave the road and to park the vehicle. But then, after immobile shutdown, the system will prevent the vehicle from being restarted until the BAC monitoring device is reset, as by an authorized person on site or remote authorized authority.

The system can include a digital camera, added to the wheel module, or aimed toward the operator from another location in the vehicle operator's location but controlled by the system. The system can included a GPS (Global Positioning System) sensor of commercially available type to record position of the vehicle, as might be useful or necessary for vehicle location if the vehicle operator is warned to quickly, and safely, park the vehicle by the BAC monitoring device. One or more random access memories (RAMs) can be useful in the system to save the BAC data, and data showing BAC vs. time, image data, and GPS data for review or evidence use.

In view of the foregoing description of the present invention, preferred embodiment and various embodiments and various methods it will be seen that the several objects of the invention are achieved and other advantages are attained.

The embodiments and/or examples that were chosen and described best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

The breadth and scope of the present invention should not be limited by any of the above-described exemplary embodiments, but instead should be defined only in accordance with the following claims appended hereto and their equivalents.

The invention claimed is:

1. A vehicle operator monitoring system for installation in a vehicle and responsive to sensing of ethanol in the body of an operator of the vehicle, comprising:

an ethanol vapor collection device oriented to collect moisture epidermally present on the palms of hands of the vehicle operator, for determining from said moisture the presence of ethanol in the body of the operator, a control module separate from the ethanol vapor collection device, the control module being configured to continuously control one or more vehicle functions including disabling the vehicle after a predetermined time, in accordance with the presence of ethanol in the body of the operator, the ethanol vapor collection device comprising a layer of moisture pervious material for receiving the moisture, a source of partial vacuum for drawing the moisture through the pervious material, so as to cause the received moisture, with any ethanol in the moisture, to be deposited on the pervious material, a moisture vapor extraction conduit for receiving the moisture vapor, with any ethanol in the moisture vapor, and providing it to the control module for ethanol analysis from which to determine blood alcohol content (BAC) of the operator, the control module providing a signal concerning at least one operation of the vehicle in response to the determination of a determined level of blood alcohol content of the vehicle operator, that signal including an announcement to the operator of a period of time in which the operator has to park the vehicle safely wherein the control module controls a digital image camera aimed at the operator and wherein the camera Is configured to take a digital image of the operator if the operator lifts either hand from a respective ethanol vapor collection device, and, wherein the control module monitors the BAC ethanol level periodically in normal operation, but, more frequently than, in said normal operation if tire BAC trends higher, but less frequently than in said normal operation, if the BAC trends lower.

2. A system as set forth in claim 1 wherein the moisture epidermally present on the palms of hands of a vehicle operator is palmar sweat of the operator.

3. A system as set forth in claim 1 wherein the porous material is a layer of high-efficiency particulate air filtration media.

4. A system as set forth in claim 1 wherein a palm shield having apertures therein overlies the porous material, such that received moisture will pass through the apertured palm shield and will be deposited as received moisture upon the filter material, and the received moisture will include any ethanol in the moisture resulting from the consumption of ethanol by the operator.

5. A system as set forth in claim 2 wherein the ethanol vapor collection device includes a contact surface for receiving the hands of the operator when driving.

6. A system as set forth in claim 5 wherein the ethanol vapor collection device includes an enclosure enclosing the moisture pervious material.

7. A system as set forth in claim 6 wherein the ethanol, vapor collection device enclosure is selectively affixed to the steering wheel in an orientation for receiving an operator's hand when driving.

8. A system as set forth in claim 7 wherein the ethanol vapor collection device enclosure is one or the other of a pair of such enclosures selectively so affixed to the steering wheel in such a way that each hand of the operator mill be in contact with one such enclosure when the operator is using the steering wheel while driving.

9. A system as set forth in claim 5 in which the ethanol vapor collection device includes a thermostatically controlled heater, when operative in response to decrease in temperature within the vehicle, to produce heating of the contact surface to enhance palmar sweating by the operator, so as to cause increased painter sweating of the operator when there is heating by the heater.

10. An apparatus, comprising an ethanol vapor collection device and a control module in signal communication with said ethanol vapor collection device, wherein the control module is configured to control one or more immobile vehicle operations, the control module is responsive to moisture collected by the ethanol vapor collection device, the presence of any measurable ethanol in the collected moisture is representative of a blood alcohol content (BAC) of an operator of the vehicle as determined by an alcohol sensor detection module located within the control module, wherein the control module is configured to cause disabling of the vehicle if tire measurable ethanol in the collected moisture exceeds a preset threshold, and wherein the control module controls a digital image camera aimed at the operator and wherein the camera is configured to take a digital image at the operator if the operator lifts either hand from a respective ethanol vapor collection device, and wherein the control module monitors the BAC ethanol level periodically in normal operation, but more frequently than in said normal operation if the BAC trends higher but less frequently than in said normal operation if the BAC trends lower.

11. The apparatus of claim 10 wherein a contact surface of each ethanol vapor collection device is electrically sensitive to the presence or absence of palm contact so as to signal it the operator lifts either hand from a respective ethanol vapor collection device.

12. The apparatus of claim 10 further comprising a heart rate detection module located within the control module.

13. The apparatus of claim 10 further comprising an air oxygen level detection module located within the control module.

* * * * *